United States Patent [19]

Castel

[11] Patent Number: 5,020,359

[45] Date of Patent: Jun. 4, 1991

[54] MEASURING METHOD AND DEVICE FOR DETERMINING A PUMPING CHARACTERISTIC OR A PARAMETER OF A FLUID

[75] Inventor: Yvon Castel, Croissy sur Seine, France

[73] Assignee: Institut Francais du Petrole, Rueil Malmaison, France

[21] Appl. No.: 374,151

[22] Filed: Jun. 30, 1989

[30] Foreign Application Priority Data

Jun. 30, 1988 [FR] France ................................. 88 08886

[51] Int. Cl.$^5$ .............................................. G01N 7/14
[52] U.S. Cl. ..................................... 73/61 R; 73/19.1
[58] Field of Search ..................... 73/61 R, 61.1 R, 19

[56] References Cited

U.S. PATENT DOCUMENTS

| | | | |
|---|---|---|---|
| 3,911,256 | 10/1975 | Jones | 73/61 R X |
| 3,968,678 | 7/1976 | Krener et al. | 73/19 |
| 4,373,374 | 2/1983 | Bajard | 73/19 |
| 4,496,287 | 1/1985 | Nelson et al. | 73/61 R X |
| 4,700,561 | 10/1987 | Dougherty | 73/61 R X |
| 4,747,300 | 5/1988 | Nelson et al. | 73/61 R |

FOREIGN PATENT DOCUMENTS 611137 6/1978 U.S.S.R. .............................. 73/61 R

*Primary Examiner*—Hezron E. Williams
*Assistant Examiner*—Joseph W. Roskos
*Attorney, Agent, or Firm*—Antonelli, Terry, Stout & Kraus

[57] ABSTRACT

A measuring method and device are provided for determining at least one pumping characteristic, or a parameter, of a fluid having at least a liquid phase and a multiphase gas phase, with the parameter being the parameter called GLR which corresponds to the ratio of the volume of the gas phase to the volume of the liquid phase. The device comprises a positive-displacement pump, having a suction pressure, a delivery pressure and a chamber having a volume, as well as one of at least one of a pressure sensor in the chamber, a detector adapted for measuring pump work, and a sensor for knowing a volume of the chamber. The sensors and detectors each deliver a value, and the characteristic to be determined is a characteristic which is not measured by the device.

18 Claims, 2 Drawing Sheets

MEASURING METHOD AND DEVICE FOR DETERMINING A PUMPING CHARACTERISTIC OR A PARAMETER OF A FLUID

BACKGROUND OF THE INVENTION

The invention relates to a measuring device and method for determining the amounts of gas and liquid in a fluid by a variation of volume in a positive-displacement pump as well possibly as physical characteristics or values of these characteristics of the fluid subjected to this variation of volume.

The invention applies in particular to the production of hydrocarbons comprising a multi-phase gas-liquid mixture, such production being carried out in particular, but not exclusively, in an environment which is difficult of access, for example at the level of an underwater well head or transfer line, or else in the virgin forest.

The invention also applies to the chemical or petroleum industry or generally to all industries using multi-phase fluids.

The invention applies advantageously to the transfer of multi-phase fluids, particularly when such transfer is effected by means of a positive-displacement pump.

Physical measurements of a fluid comprising a liquid phase and a gas phase are made for determining the relative amount of each phase. However, such measurements are made from a sample which is generally not representative of the fluid. These measurements are made in the laboratory which requires a certain delay before the results are available. These measurements are obtained, for example, during distillations, from pressure or temperature variations.

By GLR, or value of the parameter GLR, is meant the value of the ratio of the volume of gas to the volume of liquid in a fluid, this ratio being given under fixed pressure and temperature conditions.

A characteristic value is the number which quantifies one of the characteristics of a physical phenomenon. The assembly of characteristics mathematically translates all the possible configurations of a phenomenon.

To overcome the drawbacks of the above mentioned prior techniques, the present invention provides a method and device for obtaining in particular the GLR.

SUMMARY OF THE INVENTION

In accordance with the invention, a variation of volume is produced and one or more values of one or several characteristics of this variation of volume are measured so as to determine the GLR and/or other physical characteristics related to this variation of volume.

The invention takes advantage of the fact that it has been noted that a fluid comprising a liquid phase and a gas phase, which is subjected to a variation of volume, in this case compression in a positive-displacement pump, such as a piston pump, has a number of readily measurable physical characteristics developing directly in relation with the parameter GLR. In fact, for example, development of the pressure of the fluid in the chamber of the pump as a function of the volume of the chamber depends on GLR. Similarly, the work required for obtaining a certain increase of pressure or a certain reduction of volume depends on the GLR.

The set of characteristics which jointly occur with a variation of volume of a multi-phase fluid may, for example, include the suction and delivery pressures, the temperatures of the fluid on the suction side and on the delivery side, the solubility of the gas phase in the liquid phase.

In addition it has been noted that in practice an increase of pressure of a fluid with low GLR corresponds to an isotherm evolution of the gas whereas a pressure increase of a fluid with high GLR corresponds to an adiabatic evolution of the gas.

The invention provides then a measuring method for determining at least one pumping characteristic, or a parameter, of a fluid having at least a liquid phase and a gas phase, the volume of the gas phase related to the volume of the liquid phase defining a parameter called GLR.

The method of the present invention comprises the steps of introducing the fluid into a chamber of a positive-displacement pump, with the pump having a suction pressure, a delivery pressure, and a variable volume, causing a varying of a volume of the chamber, establishing at least one relationship between physical characteristics associated with the variation of volume and possibly the parameter GLR, with the characteristics each taking on values during the variation of volume, measuring, during the variation of volume, at least one of the values of one of the characteristics, and from the relationship and the measured value, determining other values of the characteristics and/or the parameter GLR are determined.

The characteristics may be chosen from, for example, a pressure prevailing in the pumping chamber, energy producing a variation of volume, and a volume or volumes of the pumping chamber.

The relationship may be established by calibration from a sample of the fluid.

A piston pump may be used as positive-displacement pump.

The suction and/or delivery pressure and/or temperature of the pump may be measured.

An automatic device may be used for storing the relationship and determining one at least of the values which has not been measured and/or the parameter GLR, such determination being obtained by introducing measured values into the automatic device.

The relationship may be a continuous function.

Knowing the respective masses per unit of volume of the liquid phase and of the gas phase, the flowrate per unit mass of the fluid transiting through the chamber of the pump may be determined.

The chamber having at least one mobile wall, the volume of the chamber may be determined from the position of the mobile wall.

The variation of volume may be a reduction of volume.

For a given volume of the chamber, the associated value of the pressure may be measured so as to determine a parameter representative, at least partially, of the fluid composition, such as the parameter GLR.

For a given volume of the chamber, the value of the energy may be measured so as to determine a parameter representative, at least partially, of the composition of the fluid, such as said parameter GLR.

For a given value of the pressure in the chamber, the value of the associated volume may be measured so as to determine a parameter representative, at least partially, of the composition of the fluid such as the parameter GLR, and/or the value of the energy required for obtaining the given pressure value.

The invention further provides a measuring device for determining at least one pumping characteristic, or a parameter, of a fluid having at least a liquid phase and a gas phase, the parameter being the parameter called GLR which corresponds to the ratio of the volume of the gas phase to the volume of the liquid phase.

This device is particularly characterized in that it comprises a positive-displacement pump, having a suction pressure and a delivery pressure and comprising a chamber having a volume, and in that this device further comprises one at least one pressure sensor in the chamber, detector adapted for measuring pumping work, and sensor for knowing the volume of the chamber.

With these elements each delivering a value, the characteristic to be determined is a characteristic which is not measured by the device.

The chamber having at least one mobile wall, the volume sensor of the chamber may be a sensor detecting the position of the mobile wall.

The position sensor may be a linear sensor.

The position sensor may be an angular sensor.

The positive-displacement pump used in the method of the invention, or forming part of the device of the invention, may be used for transporting fluid through a duct.

The method or the device may be applied to the determination of pumping characteristics or of he parameter called GLR of a fluid comprising at least hydrocarbons.

BRIEF DESCRIPTION OF THE DRAWINGS

The invention will be well understood from the following description of a non limitative example, illustrated by the accompanying figures in which.

DESCRIPTION OF THE PREFERRED EMBODIMENTS

Figure 1:
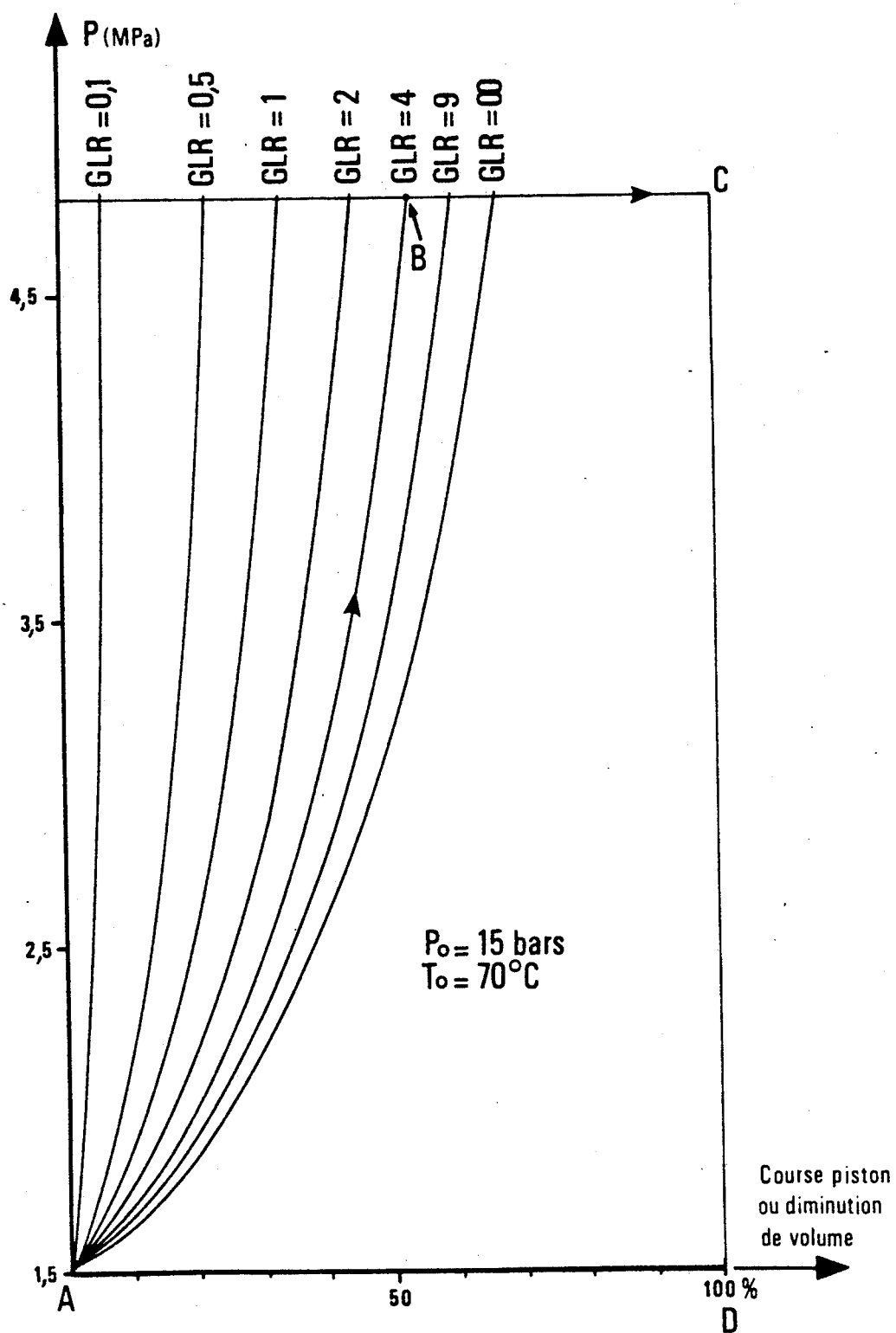
FIG. 1 is a graphical illustration of the influence of the GLR of a fluid on the evolution of the pressure as a function of a volume compression for a piston pump.

FIG. 1 shows the evolution of the pressure within a fluid as a function of the variation of volume of a piston pump for different GLRs of a fluid. The fluid which is a multi-phase fluid comprises a gas phase consisting of a perfect gas and a liquid phase consisting of an incompressible liquid.

The values of the absolute pressure are given in ordinates, whereas the stroke of the piston or variation of volume of the chamber during the pumping sequence is shown in abscissa by a relative scale 0–100%.

Since the positive-displacement pump considered is a piston pump with linear displacement and since, consequently, the surface of the mobile portion of the chamber has a constant area, it may be considered that the variation of volume of the chamber is proportional to the stroke of the piston.

Considering in particular the law of perfect gases $PV_g = nRT_g$ becoming $PV_g = $ constant in the case of an isotherm transformation, P being the pressure to which the volume of gas $V_g$ is subjected at the absolute temperature $T_g$ of the gas, R being the constant of perfect gases, the volume of liquid $V_l$ being invariable, the GLR defined under the initial compression conditions by the ratio of the volume of gas to the volume of liquid $GLR = V_g/V_l$, the volume of the pumping chamber $V_c = V_g + V_l$ at each moment of the pumping, the initial pressure Po being equal to 1.5 MPa and the temperature equal to the initial temperature To of 70° C., i.e. 343K, the network of curves of FIG. 1 is obtained by calculation.

For a given GLR, for example GLR=4, the evolution of the pumping characteristics, such as the pressure and the volume, is shown by the curve AB, then by the segment BC. The curve AB corresponds to a compression sequence whereas the segment BC corresponds to a transfer of the fluid from the compression chamber to a reservoir or a duct whose pressure is kept constant. With a view in particular to preventing any fluid backflow, the pump is provided with a valve having an opening pressure. This opening pressure is equal to the delivery pressure of the pump.

The area of the surface defined by curve AB and segments BC, CD and DA is proportional to the work required for pumping the fluid having, for this position of point B on the isobar passing through point C, a GLR=4. It will then be noted that the pumping work, for given suction and delivery pressure conditions, a given initial temperature, etc. is a strictly decreasing function of the GLR.

According to the invention, if the suction pressure Po and the temperature of the fluid on the suction side are not known, they are measured so as to determine the network of curves depending on the GLR (or more generally on a parameter representative, at least partially, of the composition of the fluid), or by calculation as for the curves shown in FIG. 1, or by physical measurements, or by these two means at the same time. For the curves obtained by calculation, other interfering parameters may be introduced for determining them, for example, parameters relative to the solubility of the gas in the liquid, to the compressibility of the liquid, to the change of state, to the real behavior of the gas.

To determine the curves, it is also possible to take into account the heat and dynamic exchanges between the liquid and gas phases in the pumping chamber.

Knowing the evolution of the pressure, volume variation or piston stroke characteristics, for different parameters GLR and for a given pump, it is possible to determine a characteristic or the parameter the GLR from one or more measurements.

A particular interest of the invention is to determine the GLR. For that, it is sufficient to determine the value of the pressure for a given stroke value of the piston or the value of the stroke of the piston so as to obtain a given pressure value, or the value of the stroke for which the transfer of the fluid is effected, or the variation of pressure associated with a stroke variation, or the value of the work provided so as to obtain a given value of the pressure or of the stroke, or the values of the pressure or of the stroke so as to obtain a given amount of work . . . .

Such determination of the GLR may be provided by means of a graph, by computation software, or by means of a microprocessor in which are written the relations relating the different parameters and characteristics, either in discrete form, or in continuous form, or else by reading out a corrected measurement as may happen after calibration and with the use of a single sensor. Thus, a value of the GLR corresponds to a measurement of the value of the stroke required for obtaining a certain pressure.

In a variant of the method of the invention, if several different measurements are made, such as two pressure measurements associated with two stroke measurements, it is possible to determine an unknown characteristic value, thus the suction temperature can be determined.

According to the invention, all sorts of positive-displacement pumps can be used, such for example as: linear piston pumps, rotary piston pumps, pumps with internal or external gears, load pumps, pumps with pivoting or sliding blades, screw, cam and piston pumps ....

According to the invention, the knowledge or the measurement of the amount of work for obtaining a certain variation of volume of the fluid makes it possible to determine the parameter GLR or any other unknown compression characteristic. Such pumping work may be determined from the measurement of the energy consumed by the drive means of the pump and from the value of the mechanical efficiency of the pump.

For a linear piston pump producing an increase of the pressure of a certain mass of fluid, the pumping energy corresponds to the energy absorbed by the pump for increasing the pressure of the fluid but not to the energy absorbed by the pump for introducing the fluid into the chamber. To permit measurements of the compression energy to be obtained, the chamber may be equipped with pressure sensors or sensors detecting displacement of the piston.

Figure 2:
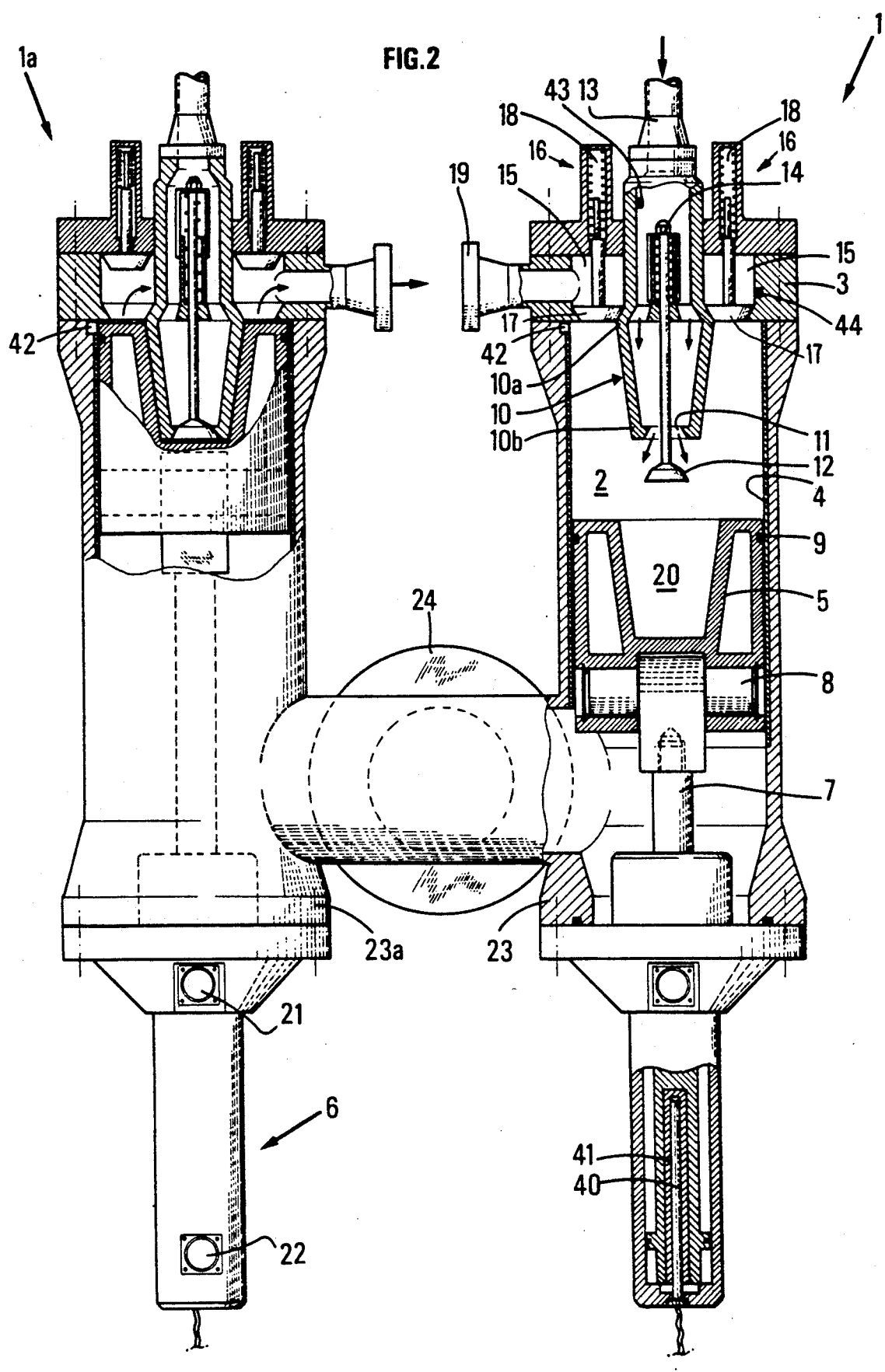
FIG. 2 is a partial cross-sectional view of a piston pump equipped with a device of the invention.

FIG. 2 shows a pumping unit for petroleum effluents provided with the measurement device of the invention for implementing the above method.

Reference 1 designates as a whole a first pumping element comprising the device of the invention, reference 1a being relative to a second pumping element of this unit identical to the first element.

This first pumping element 1 comprises a chamber 2 defined by a cylinder head 3, a cylinder 4 and a piston 5. Piston 5 slides in a cylinder 4 driven by a jack 6 coupled by rod 7 to jack 6 and a shaft 8. The piston comprises sealing means 9, such as piston rings, or lipped seals used for example in mud pump pistons, which cooperate with cylinder 4 to provide compression of the fluid. The cylinder head 3 comprises a projection 10 situated along the axis of the cylinder, this projection having a truncated cone shape opening out at its base 10a and a fluid supply orifice 11 at its top 10b. The supply orifice 11 comprises a seat which is closed by a valve 12 during the filling phase of chamber 2, so as to let the fluid penetrate therein from the supply duct 13.

The fluid penetrates into the chamber because of the difference of pressure forces existing on each side of valve 12 and which is sufficient to oppose the return means 14 of valve 12. The fluid, which is compressed by reduction of the volume of chamber 2, escapes from chamber 2 through four discharge orifices 15 provided with non return valves 16 comprising valves 17 which cooperate with seats integral with the cylinder head and springs 18 providing closure of the discharge orifices during the supply phase of chamber 2. The discharge orifices 15 are connected to a discharge duct 19.

During reduction of the volume of chamber 2, projection 10 penetrates into housing 20 of the piston so as to produce a jet of fluid directed towards the discharge orifices 15. The substantially complementary and truncated cone shapes of housing 20 and projection 10 permit the production of a high speed jet on the walls of housing 20 of piston 5, of cylinder head 3 (particularly its projection 10) and cylinder 4, so as to facilitate discharge of the fluid and cleaning of the deposits which would become encrusted thereon without this advantageous arrangement. The central arrangement of projection 10 and housing 20 further permits distribution of the fluid, promoting compression thereof, as soon as it is introduced into the chamber.

Jack 6 is connected through two orifices 21 and 22 to hydraulic generators adapted for causing the movements of the jack and variations of the volume of chamber 2.

Element 1 of the pumping device further comprises a casing, designated as a whole by reference 23, which surrounds the space swept by piston 5 and opposite chamber 2 with respect to piston 5, as well as the free space between the piston and the body or fixed portion of jack 6.

This casing 23 communicates with the similar casing 23a of the pumping element 1a. The casings 23, 23a, ... of the different elements contain a gaseous fluid whose pressure is in particular adapted to reduce, even cancel out, the leaks of multi-phase fluid between chamber 2 and the casing, and/or to reduce the thickness of the casing(s) 23, 23a, ... which might have to withstand the hydrostatic pressure of the medium surrounding the pumping device. Thus, in underwater oil working, this external pressure may be that produced by a sea-water column of 1000 m in height.

Often very advantageously, this pressure may be that of the supply duct, or that of the delivery duct.

The casing may be connected to, even have passing therethrough, one or other of these ducts. The fluid leaks between chamber 2 and casing 3 may then be mixed with the fluid which is being pumped or is to be pumped.

Jack 6 comprises a linear position sensor comprising a fixed portion 40 fast with the body of the jack and a mobile portion 41 fast with the rod of the jack. This position sensor may be an inductance variation sensor or a resistance variation sensor or else a mutual inductance variation sensor.

The speed sensors, such as the Digital Linear Displacement Measuring System of the firm Sacol Powerline, associated with electronic means for processing the information, allow the position of the rod 7 of the jack to be known accurately with respect to the cylinder 4 and thus the volume of the pumping chamber 2.

These sensors comprise a mobile portion 41 formed of a succession of looped coils and a fixed portion comprising two energization coils and a detection coil connected by wires to the processing system.

The upper portion of the pumping chamber 2 comprises a pressure sensor 42 to which the fluid is subjected. The fluid supply duct 13 comprises a temperature sensor 43 for controlling the initial temperature of the fluid and so for taking into account its modification for determining the GLR or other parameters.

In practice, the temperature of the effluents of an oil well is constant when the production is constant, and decreases when the effluent production increases.

Furthermore, a temperature sensor 44 is disposed in the discharge orifices 15. This sensor 44 provides fine evaluation of the high GLRs by carrying out correlations with isotherm, adiabatic or polytropic transformations.

For pumps having a rotary member with variation of volume of the chamber, an optical angular position sensor may be used.

In underwater oil production in particular, knowledge of the GLR at the level of a pump situated upstream of a processing platform makes it possible to adapt beforehand the processing apparatus, for example, for using additional separators or by a different arrangement of a separator better adapted to a fluid having a certain GLR.

The pumping energy may be determined during the fluid compression sequence by measuring the pressure in jack 6. This measurement may be made at the same time as that of the stroke of piston 6. For pumps driven by an electric motor, a wattmeter may be used for determining this pumping energy.

What is claimed is:

1. A measuring method for determining at least one of a pumping characteristic and a parameter of a multi-phase fluid having at least a liquid phase and a gas phase, a volume of the gas phase being related to a volume of the liquid phase defining a parameter GLR, the method comprising the steps of:
   introducing said fluid into a chamber of a positive-displacement pump having a suction pressure, a delivery pressure, and a variable volume,
   causing a variation of the volume of said chamber,
   establishing at least one relationship between physical characteristics associated with at least one of said variation of volume and said parameter GLR, said characteristics each taking on values during the variation of volume of said chamber,
   measuring at least one of said values of one of said physical characteristics during a transfer of said multi-phase fluid, and
   determining from said relationship and said measured value other values of at least one of the physical characteristics and said parameter GLR.

2. The method as claimed in claim 1, wherein said physical characteristics include at least one of a pressure prevailing in said pumping chamber, energy producing said variation of volume, and at least one volume of said pumping chamber.

3. The method as claimed in one of claims 1 or 2, further comprising the step of storing said relationship in an automatic device and determining at least one of at least one of unmeasured values and the parameter GLR by introducing the measured values into said automatic device.

4. The method as claimed in claim 3, wherein said relationship is a continuous function.

5. The method as claimed in claim 3, further comprising the step of determining the flow rate per unit of mass of the fluid being transferred through the chamber of said pump in dependence upon determined masses per unit of volume of said liquid phase and said gas phase.

6. The method as claimed in claim 2, further comprising the step of measuring an associated value of the pressure for a given volume of the chamber so as to determine a parameter at least partially representative of the fluid composition.

7. The method as claimed in claim 2, further comprising the step of measuring a value of said energy producing the variation of said volume for a given volume of the chamber so as to determine a parameter at least partially representative of the composition of the fluid.

8. The method as claimed in claim 2, further comprising the step of measuring a value of an associated volume for a given volume of pressure in said chamber so as to determine a parameter at least partially representative of at least one of a composition of the fluid and a value of energy required for obtaining said given pressure value.

9. The method as claimed in one of claims 7 or 8, wherein the parameter at least partially representative of the composition of the fluid is the GLR.

10. The method according to one of claims 1 or 2, wherein the multi-phase fluid comprises at least hydrocarbons.

11. The method as claimed in claim 1, wherein said step of establishing at least one relationship includes calibration from the sample of the fluid.

12. The method as claimed in claim 1 wherein a piston pump is used as a positive-displacement pump.

13. The method as claimed in claim 1, wherein said physical characteristics include at least one of said suction pressure, delivery pressure and temperature of the pump.

14. The method as claimed in claim 1, wherein said chamber has at least one mobile wall, and wherein the volume of said chamber is determined from the position of said mobile wall.

15. The method as claimed in claim 1, wherein said variation of volume is a reduction of volume.

16. A measuring device for determining at least one of a pumping characteristic and a parameter of a multi-phase fluid having at least a liquid phase and a gas phase, said parameter corresponding to a ratio of a volume of the gas phase to a volume of the liquid phase, the device comprising a positive-displacement pump, a chamber having a volume, and at least one of a pressure sensor in said chamber, a detector adapted for measuring pumping work, and a sensor for sensing a volume of the chamber, wherein said detector and sensors each provide a value and said pumping characteristic to be determined is a characteristic not measured by said measuring device, and wherein said positive-displacement pump further includes a supply duct through which the multi-phase fluid is supplied and a discharge duct from which the multi-phase fluid is discharged whereby a measuring is effected during a transfer of the multi-phase fluid from the supply duct to the discharge duct.

17. The device as claimed in claim 16, wherein said chamber has at least one mobile wall, and wherein said sensor for sensing the volume of the chamber is a sensor detecting a position of the mobile wall and being constructed as one of a linear sensor and an angular sensor.

18. As claimed in one of claims 16 or 17, wherein the multi-phase fluid comprises at least hydrocarbons.

* * * * *